United States Patent [19]

Lorenz et al.

[11] 4,321,396
[45] Mar. 23, 1982

[54] COPOLYMERIZABLE, ULTRAVIOLET LIGHT ABSORBER ALLYLOXY-2-(2H-BENZOTRIAZOL-2-YL)-4-ALKYLBENZENES

[75] Inventors: Donald H. Lorenz, Basking Ridge, N.J.; Bruce A. Gruber, Worthington, Ohio

[73] Assignee: GAF Corporation, New York, N.Y.

[21] Appl. No.: 215,196

[22] Filed: Dec. 10, 1980

Related U.S. Application Data

[62] Division of Ser. No. 112,882, Jan. 17, 1980, abandoned.

[51] Int. Cl.$^3$ .......................................... C07D 249/20
[52] U.S. Cl. ..................................... 548/260; 526/259
[58] Field of Search ........................................ 548/260

[56] References Cited

U.S. PATENT DOCUMENTS 3,072,585  1/1963  Milionis et al. ..................... 548/260
3,218,332  11/1965  Heller et al. ....................... 548/260

*Primary Examiner*—Paul M. Coughlan, Jr.

*Attorney, Agent, or Firm*—James Magee, Jr.; Walter Katz

[57] ABSTRACT

This invention relates to copolymerizable ultraviolet light absorber compounds having the formula:

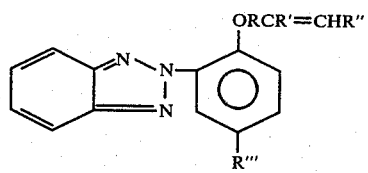

where
R is alkylene, $C_1$–$C_{10}$, oxyalkylene, $C_1$–$C_{10}$, alkyleneoxyalkylene, $C_1$–$C_{10}$ or phenylene, $C_1$–$C_{10}$, unsubstituted or substituted with hydroxy;
R' and R" are independently hydrogen or alkyl; $C_1$–$C_6$; and
R'" is hydrogen or alkyl, $C_1$–$C_6$.

1 Claim, No Drawings

COPOLYMERIZABLE, ULTRAVIOLET LIGHT ABSORBER ALLYLOXY-2-(2H-BENZOTRIAZOL-2-YL)-4-ALKYLBENZENES

This is a division of application Ser. No. 112,882, filed Jan. 17, 1980, now abandoned.

BACKGROUND OF THE INVENTION

1. Field of the Invention

This invention relates to novel copolymerizable ultraviolet light absorber compounds, and, more particularly, to allyloxy-2-2H-benzotriazol-2-yl)-4-alkylbenzene compounds which are copolymerizable with vinyl monomers to provide polymer materials having improved resistance to degradation to light.

2. Description of the Prior Art

Various organic compounds exhibit the power to absorb electromagnetic radiation and can be incorporated in various plastic materials such as transparent sheets which act as filters for all the radiation passing through and will transmit only such radiations as are not absorbed by the sheet and/or the absorbing agent. Such filters find use in many technical and commercial applications.

Numerous cyano acrylic compounds have been suggested as absorbents for the range of radiations described above. For specific compounds, see U.S. Pat. Nos. 3,081,280; 3,272,810; 3,644,466; 3,256,312; and 3,215,724. These ultraviolet absorbers are mechanically mixed with the plastic materials to prevent discoloration and degradation of the material. However, it has been observed that such absorbers sometimes fail or are blocked out of the plastic under adverse weather conditions before the lifetime of the protected material. Also, it is not possible to use all of these ultraviolet absorbers with radiation curing of the plastic material. Another disadvantage of these ultraviolet absorbers is the high amount of absorber needed for protection of some materials.

Accordingly, it is an object of the present invention to provide novel copolymerizable ultraviolet light absorber compounds which are substantially free of the disadvantages of the prior art.

A particular object of this invention is to provide novel compounds which can be copolymerized directly with monomers, such as plastic material, to provide more permanent ultraviolet light protection.

A specific object is to provide ultraviolet light absorber compounds containing a copolymerizable ethylenic group.

These and other objects and features of the invention will be made apparent from the following more particular description of the invention.

SUMMARY OF THE INVENTION

What is provided herein are improved, novel copolymerizable ultraviolet light absorber compounds of the formula:

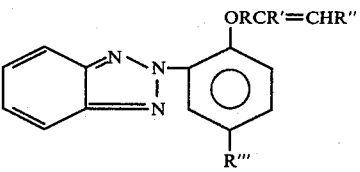

where

R is alkylene, $C_1-C_{10}$, oxyalkylene, $C_1-C_{10}$, alkyleneoxyalkylene, $C_1-C_{10}$ or phenylene, $C_1-C_{10}$, unsubstituted or substituted with hydroxy, R' and R" are independently hydrogen or alkyl, $C_1-C_6$, and R''' is hydrogen or alkyl, $C_1-C_6$.

In the best mode of the invention, R is alkylene, $-CH_2-$, R' and R" are both hydrogen, and R''' is $-CH_3$.

DETAILED DESCRIPTION OF THE INVENTION

The compounds of the invention contain ultraviolet light absorber and copolymerizable portions in the same molecule. These portions are effectively separated so that each can perform its own function without interference from the other. Therefore, the absorber portion does not inhibit the copolymerization, and the ethylenic radical does not effect the light absorbing properties of the molecule.

The $-RCR'=CHR''$ radical is copolymerizable with vinyl monomers so that the ultraviolet absorber becomes an integral part of the polymer. Suitable radicals are allyl, crotyl, methylpropenyl, vinylbenzyl, vinyloxyethyl, allyloxy-2-hydroxypropyl, and 2-hydroxy-3-butenyl. The best mode is represented by allyl. The novel compounds of the invention may be prepared, e.g. from 2-(2H-benzotriazol-2-yl)-4-alkylphenol, by alkylation with an ethylenic halide.

The novel compounds of this invention are colorless solids which are insoluble in water. The benzotriazol-2-yl chromophore of the compounds herein have an ultraviolet absorbance peak at about 290-300 nm, but no visible absorbance.

The flow sheet below illustrates the reaction sequence for preparing the compounds of the invention.

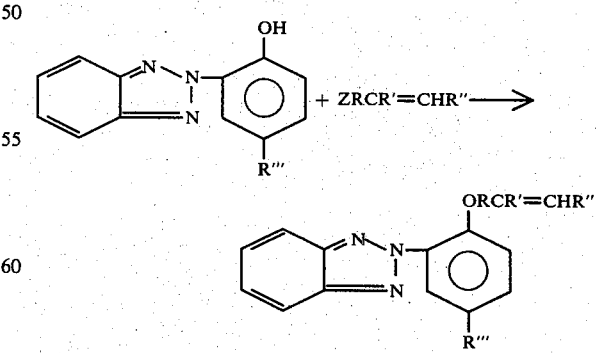

where Z is a halide and R', R" and R''' are as defined above.

Representative $-RCR'=CHR''$ radicals are $-CH_2-CH=CH_2$ (allyl), $-CH_2CH=CHCH_3$ (crotyl), —CH$_2$C(CH$_3$)=CH$_2$ (2-methyl-1-propenyl),

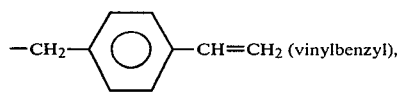 (vinylbenzyl),

—CH$_2$CH$_2$OCH=CH$_2$ (vinyloxyethyl),

—CH$_2$CH(OH)CH$_2$OCH$_2$CH=CH$_2$, (3-allyloxy-2-hydroxypropyl, and —CH$_2$CH(OH)CH=CH$_2$ (2-hydroxy-3-butenyl).

The alkylation of the phenol is carried out with a reactive ethylenic compound, such as an ethylenic halide, e.g. allyl chloride or allyl bromide. The reaction is carried out in an inert solvent, such as acetone, at a suitable temperature, generally at the reflux temperature of the solvent, for about 24 hours. The reactants are controlled to provide at least a 1:1 molar ratio of the ethylenic halide to the phenol compound.

The compounds of the invention may be copolymerized, for example, with monomers and oligomers by conventional free radical polymerization or with radiation curing, if desired, to provide useful polymeric coatings, or formulated into cosmetic preparations, such as skin and hair care products.

The following examples will describe the invention with more particularity.

EXAMPLE 1

Allyloxy-2-(2H-Benzotriazol-2-Yl)-4-Methylbenzene

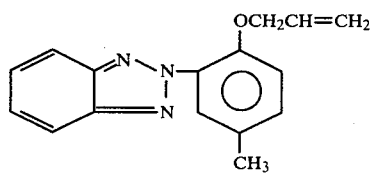

Into a flask equipped with a magnetic stirrer and reflux condenser is charged 11 g of 2-(2H-benzotriazol-2-yl)-4-methylphenol, 300 ml acetone, 14 g potassium carbonate and 6.2 g (0.05 moles) of allyl bromide. The suspension is heated at reflux for 24 hours; then 300 ml water is added. Upon cooling an oil separates that quickly crystallizes. The solid is filtered giving a high yield of the desired product;

EXAMPLE 2

Crotyloxy-2-(2H-Benzotriazol-2-Yl)-4-Methylbenzene

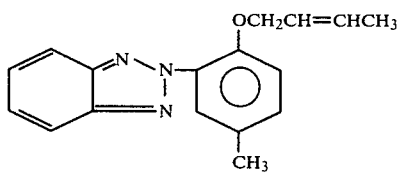

When crotyl bromide was substituted for allyl bromide in Example 1, the desired product is obtained.

EXAMPLE 3

(2'-Methylpropenyl)oxy-2-(2H-Benzotriazol-2-Yl)-4-Methylbenzene

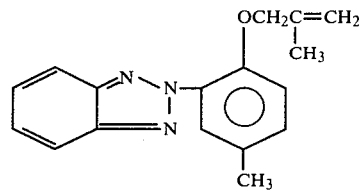

When 3-chloro-2-methyl-1-propene was substituted for allyl bromide in Example 1, the desired product is obtained.

EXAMPLE 4

4'-Vinylbenzyloxy-2-(2H-Benzotrial-2-Yl)-4-Methylbenzene

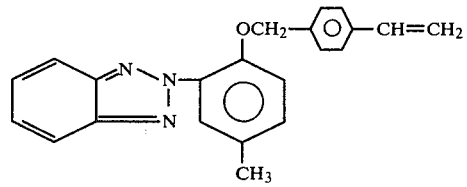

When vinylbenzyl chloride was substituted for allyl bromide in Example 1, the desired product is obtained.

EXAMPLE 5

(Vinyloxyethyl)oxy-2-(2H-Benzotriazol-2-Yl)-4-Methylbenzene

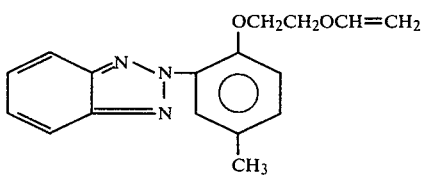

When vinyloxyethyl chloride was substituted for allyl bromide in Example 1, the desired product is obtained.

EXAMPLE 6

(3'-Allyloxy-2'-Hydroxypropyl)oxy-2-(2H-Benzotriazol-2-Yl)-4-Methylbenzene

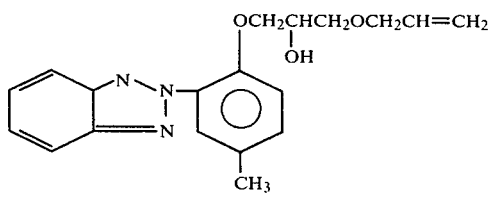

When 0.1 moles of the phenol of Example 1 and allyl glycidyl ether, and, 250 mg. of tetramethylammonium chloride are heated at 150° C. for 16 hrs., diluted with 50 ml. methylene chloride, decolorized, filtered, and evaporated the desired product is obtained.

EXAMPLE 7

(2'-Hydroxy-3'-Butenyl)oxy-2-(2H-Benzotriazol-2-Yl)-4-Methylbenzene

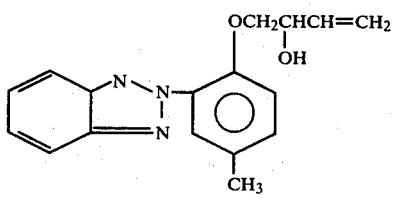

When 2-hydroxy-3-butenyl bromide was substituted for allyl bromide in Example 1, the desired product was obtained.

EXAMPLE 8

The monomer compound of Example 1 is copolymerized with another monomer by charging a flask with 150 ml ethanol, 1.5 g allyloxy-2-(2H-benzotriazol-2-yl)-4-methylbenzene and a 50 g vinyl pyrrolidone. The contents are heated to 75° C. under $N_2$ and polymerization is initiated with 0.2 g azobis-isobutyronitrile (AIBN). After 1.5 hrs., another 0.2 g AIBN is added and heating is continued for another 1.5 hrs. The solvent is concentrated and added to stirred ether. A white precipitate of the copolymer is obtained which is filtered and dried, giving 18 g (36%) of product. A 5% aqueous solution of the copolymer is filtered; the ultraviolet spectra of the filtrate shows that the copolymer contains 5.8% of the absorber compound.

While certain preferred embodiments of the present invention have been illustrated by way of specific example it is to be understood that the present invention is in no way to be deemed as limited thereto but should be construed as broadly as all or any equivalents thereof.

What is claimed is:

1. A compound which is 4'-vinylbenzyloxy-2-(2H-benzotriazol-2-yl)-4-methylbenzene.